United States Patent
Soares Da Silva et al.

(10) Patent No.: US 9,604,970 B2
(45) Date of Patent: Mar. 28, 2017

(54) 1,3-DIHYDROIMIDAZOLE-2-THIONE DERIVATIVES FOR USE IN THE TREATMENT OF PULMONARY ARTERIAL HYPERTENSION AND LUNG INJURY

(71) Applicant: BIAL—PORTELA & CA S.A., S. Mamede do Coronado (PT)

(72) Inventors: Patrício Manuel Vieira Araújo Soares Da Silva, S. Mamede do Coronado (PT); Maria João Macedo Da Silva Bonifácio, S. Mamede do Coronado (PT)

(73) Assignee: Bial-Portela & CA, S.A., S. Mamede do Coronado (PT)

( * ) Notice: Subject to any disclaimer, the term of this patent is extended or adjusted under 35 U.S.C. 154(b) by 0 days.

(21) Appl. No.: 14/441,043

(22) PCT Filed: Nov. 14, 2013

(86) PCT No.: PCT/PT2013/000065
§ 371 (c)(1),
(2) Date: May 6, 2015

(87) PCT Pub. No.: WO2014/077715
PCT Pub. Date: May 22, 2014

(65) Prior Publication Data
US 2015/0299172 A1    Oct. 22, 2015

Related U.S. Application Data

(60) Provisional application No. 61/726,119, filed on Nov. 14, 2012.

(51) Int. Cl.
*A61K 31/417* (2006.01)
*A61K 31/4178* (2006.01)
*C07D 405/04* (2006.01)

(52) U.S. Cl.
CPC .......... *C07D 405/04* (2013.01); *A61K 31/417* (2013.01); *A61K 31/4178* (2013.01)

(58) Field of Classification Search
CPC . A61K 31/417; A61K 31/4178; C07D 405/04
See application file for complete search history.

(56) References Cited

FOREIGN PATENT DOCUMENTS

| WO | 2004033447 A1 | 4/2004 |
|---|---|---|
| WO | 2007081232 A1 | 7/2007 |
| WO | 2008085074 A2 | 7/2008 |
| WO | 2008136695 A1 | 11/2008 |
| WO | 2014077715 A1 | 5/2014 |

OTHER PUBLICATIONS

Filing receipt and specification for provisional patent application entitled "Therapy," by Patricio Manuel Vieira Araújo Soares da Silva, et al., filed Nov. 14, 2012 as U.S. Appl. No. 61/726,119.
Foreign communication from the priority application—International Search Report and Written Opinion, PCT/PT2013/000065, Feb. 18, 2014, 12 pages.
Galié, Nazzareno, et al., "Guidelines for the diagnosis and treatment of pulmonary hypertension," European Heart Journal, 2009, pp. 2493-2537, vol. 30, The European Society of Cardiology.
Nunes, Teresa, et al., "Pharmacokinetics and Tolerability of Etamicstat Following Single and Repeated Administration in Elderly Versus Young Healthy Male Subjects: An Open-Label, Single-Center, Parallel-Group Study," Clinical Therapeutics, XP028230640, 2011, pp. 776-791, vol. 33, No. 6, Elsevier HS Journals, Inc.
Simonneau, Gérald, et al., "Updated Clinical Classification of Pulmonary Hypertension," J Am Coll Cardiol, 2009, pp. S43-S54, vol. 54, No. 1, Suppl S, American College of Cardiology Foundation.
Irwin, Samuel, "Comprehensive Observational Assessment: la. A Systematic, Quantitative Procedure for Assessing the Behavioral and Physiologic State of the Mouse," Psychopharmacologia (Berl.), 1968, vol. 13, pp. 222-257.
Rey, Markus, et al., "Monocrotaline-Induced Pulmonary Hypertension in Wistar Rats," Current Protocols in Pharmacology, Sep. 2009, Supplement 46, pp. 5.56.1-5.56.11.
Foreign Communication from a related counterpart application—First Office Action of Chinese Application No. 201380059547.2, dated Jun. 2, 2016, with English translation, 9 pages.

*Primary Examiner* — Sahar Javanmard
(74) *Attorney, Agent, or Firm* — Conley Rose, P.C.; Rodney B. Carroll

(57) ABSTRACT

The present invention relates to compounds of formula I:

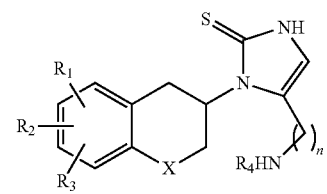

for use in treating pulmonary arterial hypertension and associated conditions, where $R_1$, $R_2$ and $R_3$ are the same or different and signify hydrogens, halogens, alkyl, alkylaryl, alkyloxy, hydroxy, nitro, amino, alkylcarbonylamino, alkylamino or dialkylamino group; $R_4$ signifies hydrogen, alkyl, -alkylaryl or -alkylheteroaryl; X signifies $CH_2$, oxygen atom or sulphur atom; n is 1, 2 or 3, with the proviso that when n is 1, X is not $CH_2$; and the individual (R)- and (S)-enantiomers or mixtures of enantiomers and pharmaceutically acceptable salts thereof.

19 Claims, 5 Drawing Sheets

FIG. 4A
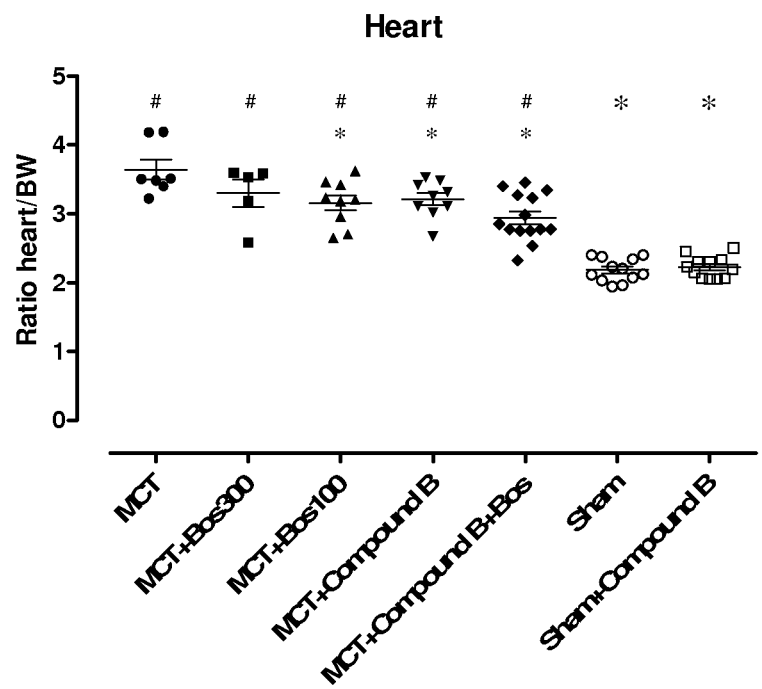
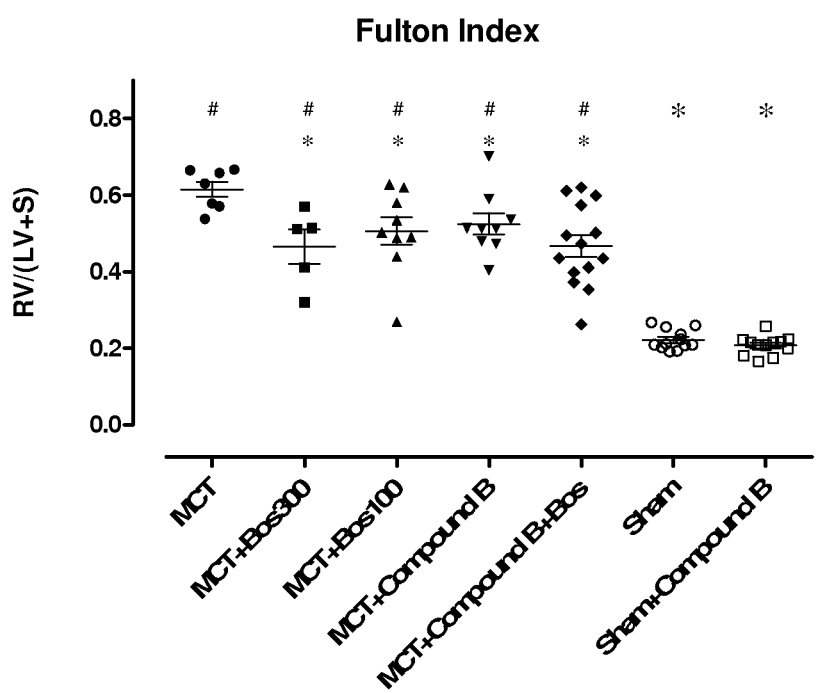
FIG. 4B

FIG. 5A
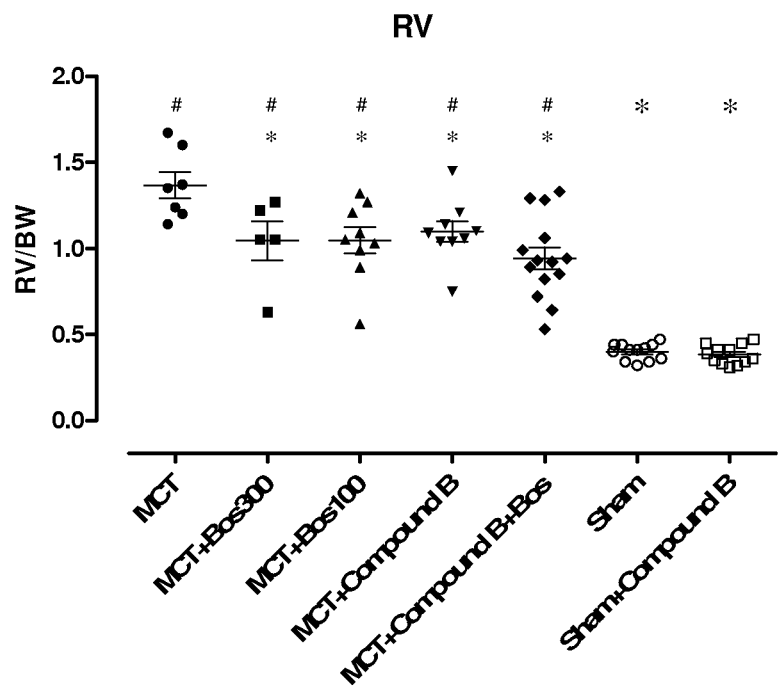
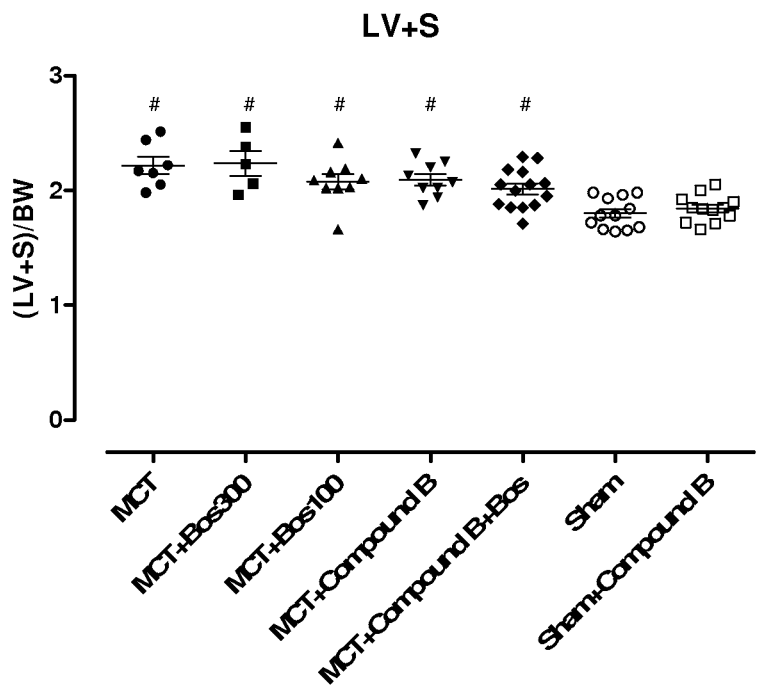
FIG. 5B

1,3-DIHYDROIMIDAZOLE-2-THIONE DERIVATIVES FOR USE IN THE TREATMENT OF PULMONARY ARTERIAL HYPERTENSION AND LUNG INJURY

CROSS-REFERENCE TO RELATED APPLICATIONS

This application is a filing under 35 U.S.C. 371 of International Application No. PCT/PT2013/000065 filed Nov. 14, 2013, entitled "1,3-Dihydroimidazole-2-Thione Derivatives For Use In The Treatment Of Pulmonary Arterial Hypertension And Lung Injury," which claims priority to U.S. Provisional Application No. 61/726,119 filed Nov. 14, 2012, entitled, "Therapy," which applications are incorporated by reference herein in their entirety.

FIELD OF THE INVENTION

The present invention relates to new therapeutic applications involving the following class of compounds of formula I:

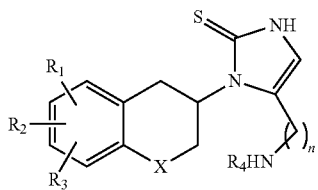

where $R_1$, $R_2$ and $R_3$ are the same or different and signify hydrogens, halogens, alkyl, alkylaryl, alkyloxy, hydroxy, nitro, amino, alkylcarbonylamino, alkylamino or dialkylamino group; $R_4$ signifies hydrogen, alkyl, -alkylaryl or -alkylheteroaryl; X signifies $CH_2$, oxygen atom or sulphur atom; n is 1, 2 or 3, with the proviso that when n is 1, X is not $CH_2$; and the individual (R)- and (S)-enantiomers or mixtures of enantiomers and pharmaceutically acceptable salts thereof.

SUMMARY OF THE INVENTION

According to a first aspect of the present invention, there is provided a compound of formula I:

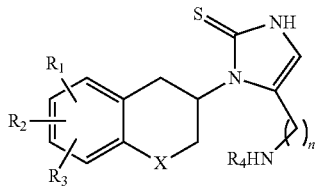

for use in treating pulmonary arterial hypertension (PAH), where $R_1$, $R_2$ and $R_3$ are the same or different and signify hydrogens, halogens, alkyl, alkylaryl, alkyloxy, hydroxy, nitro, amino, alkylcarbonylamino, alkylamino or dialkylamino group; $R_4$ signifies hydrogen, alkyl, -alkylaryl or -alkylheteroaryl; X signifies $CH_2$, oxygen atom or sulphur atom; n is 1, 2 or 3, with the proviso that when n is 1, X is not $CH_2$; and the compound of formula I includes its individual (R)- and (S)-enantiomers or mixtures of enantiomers and pharmaceutically acceptable salts thereof. The compound of formula I may be used alone or in combination with another active pharmaceutical ingredient.

In an embodiment, X is O.

In another embodiment, at least one of $R_1$, $R_2$ and $R_3$ is fluorine. Preferably, at least two of $R_1$, $R_2$ and $R_3$ are fluorine and the other is hydrogen.

Unless stated otherwise, in this specification the term alkyl (whether used on its own or used in combination with other moieties) means hydrocarbon chains, straight or branched, containing from one to six carbon atoms, optionally substituted by aryl, alkoxy, halogen, alkoxycarbonyl or hydroxycarbonyl groups; the term aryl (whether used on its own or used in combination with other moieties) means a phenyl or naphthyl group, optionally substituted by alkyloxy, halogen or nitro group; the term halogen means fluorine, chlorine, bromine or iodine; and the term heteroaryl means heteroaromatic group, wherein the heteroatoms are selected from O, N or S. Moreover, the terms 'alkoxy' and 'alkyloxy' are interchangeable, unless indicated otherwise.

Preferably, the heteroaryl group is represented by an optionally substituted aromatic heterocyclic ring system of up to 10 atoms containing one to four heteroatoms selected from N, O or S. Suitably, the heteroaryl is a heterophenyl group, and the heterophenyl includes from 1 to 4 heteroatoms, the or each heteroatom being independently selected from O, N or S. Suitably, the heteroaryl is a heteronaphthyl group, and the heteronaphthyl includes from 1 to 4 heteroatoms, the or each heteroatom being independently selected from O, N or S. Examples of preferred aromatic heterocycles of up to 10 atoms include but are not limited to benzimidazole, benzofuran, benzothiophene, benzoxazole, benzothiazole, carbazole, cinnoline, furan, imidazole, indole, indazole, isoindole, isoquinoline, isoxazole, isothiazole, oxazole, oxadiazole, oxathiazole, oxathiazolidine, phenazine, phenothiazine, phenoxazine, phthalazine, pteridine, purine, pyran, pyrazine, pyrazole, pyridazine, pyridine, pyrimidine, pyrrole, quinoline, quinoxaline, quinazoline, tetrazole, thiophene, thiadiazole, thiazole, thiopyran, triazine and triazole in all their isomeric configurations. These heterocycles may be unsubstituted. Alternatively, these heterocycles may be substituted once or several times by $C_1$-$C_6$-alkyl, $C_1$-$C_6$-alkoxy, COOH, $SO_3H$, $CONH_2$, $SO_2NH_2$, $CONH_2$, $SO_2NH_2$, thiol, hydroxyl, nitro, cyano, fluoro, chloro, bromo, iodo, $CF_3$ or $OCF_3$.

In an embodiment, the compound of formula I has the formula IA,

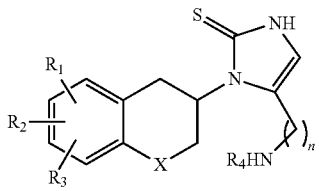

wherein $R_1$, $R_2$ and $R_3$ are the same or different and signify hydrogens, halogens, alkyl, alkylaryl, alkyloxy, hydroxy, nitro, amino, alkylcarbonylamino, alkylamino or dialkylamino group; $R_4$ signifies hydrogen, alkyl or -alkylaryl group; X signifies $CH_2$, oxygen atom or sulphur atom; n is 1, 2 or 3, with the proviso that when n is 1, X is not $CH_2$. Thus, the present invention provides a compound of formula IA for use in treating pulmonary arterial hypertension (PAH), wherein the compound of formula IA includes its (R) or (S) enantiomer, or a mixture of (R) and (S) enantiomers, and pharmaceutically acceptable salts or esters thereof.

In an embodiment, X is O.

In an embodiment, n is 2 or 3.

In another embodiment, at least one of $R_1$, $R_2$ and $R_3$ is fluorine.

In an embodiment, the compound of formula IA is (R)-5-(2-aminoethyl)-1-(6,8-difluorochroman-3-yl)-1,3-dihydroimidazole-2-thione (compound A) optionally in salt form. The compound A is suitably (R)-5-(2-aminoethyl)-1-(6,8-difluorochroman-3-yl)-1,3-dihydroimidazole-2-thione hydrochloride.

In an embodiment, the compound of formula I has the formula IB

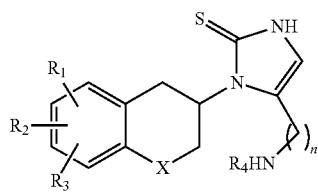

wherein $R_1$, $R_2$ and $R_3$ are the same or different and signify hydrogen, halogen, alkyl, nitro, amino, alkylcarbonylamino, alkylamino or dialkylamino group; $R_4$ signifies -alkyl-aryl or -alkyl-heteroaryl; X signifies $CH_2$, oxygen atom or sulphur atom; n is 2 or 3. Thus, the present invention provides a compound of formula IB for use in treating pulmonary arterial hypertension (PAH), wherein the compound of formula IA includes its (R) or (S) enantiomer, or a mixture of the (R) and (S) enantiomer, and pharmaceutically acceptable salts or esters thereof.

In a preferred embodiment n is 2.

In a further preferred embodiment, X is O.

Preferably $R_4$ signifies —$CH_2$-aryl or —$CH_2$-heteroaryl.

In one embodiment, the aryl group of $R_4$ is unsubstituted. The aryl group of $R_4$ may preferably be phenyl.

Desirably, one of $R_1$, $R_2$ and $R_3$ is hydrogen, and the others are fluorine.

The compound of formula I may be provided as the (R) or (S) enantiomer, or as a mixture of the (R) and (S) enantiomers in any proportions, including the racemate. The compound of formula IA and of formula IB most preferably consists of the (R)-enantiomer.

The compound may suitably be provided in the form of the hydrochloride salt. However, given the secondary aliphatic amino group, it will be obvious to the skilled technician that other acid salts can be made and are within the scope of the claimed invention.

In an embodiment, the compound of formula IB has the formula B:

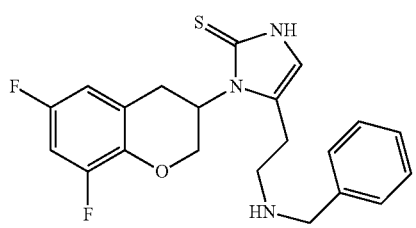

Thus, the present invention provides a compound of formula B for use in treating pulmonary arterial hypertension (PAH), wherein the compound of formula B includes its (R) or (S) enantiomer, a mixture of its (R) and (S) enantiomer, and pharmaceutically acceptable salts thereof.

The compound of formula B may be provided as the (R) or (S) enantiomer, or as a mixture of the (R) and (S) enantiomers in any proportions, including the racemate. Preferably the compound of formula B is provided as the R-enantiomer, (R)—B (compound B):

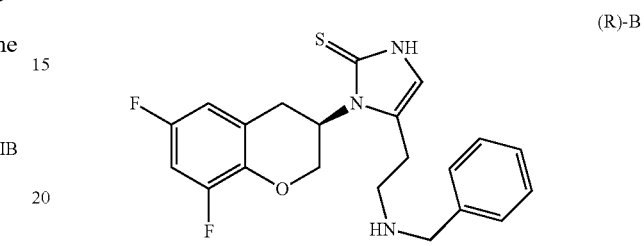

The compound of formula B (or (R)—B) is suitably provided as the hydrochloride salt. However, given the secondary aliphatic amino group, it will be obvious to the skilled technician that other acid salts can be made and are within the scope of the claimed invention.

It will be appreciated that the term "compounds of formula I" as used herein encompasses the compounds of formula I, IA, IB, B and (R)—B, and compound A.

Particular compounds of formula I for use in treating pulmonary arterial hypertension include:
(S)-5-(2-aminoethyl)-1-(1,2,3,4-tetrahydronaphthalen-2-yl)-1,3-dihydroimidazole-2-thione;
(S)-5-(2-aminoethyl)-1-(5,7-difluoro-1,2,3,4-tetrahydronaphthalen-2-yl)-1,3-dihydroimidazole-2-thione;
(R)-5-(2-aminoethyl)-1-chroman-3-yl-1,3-dihydroimidazole-2-thione;
(R)-5-(2-aminoethyl)-1-(6-hydroxychroman-3-yl)-1,3-dihydroimidazole-2-thione;
(R)-5-(2-aminoethyl)-1-(8-hydroxychroman-3-yl)-1,3-dihydroimidazole-2-thione;
(R)-5-(2-aminoethyl)-1-(6-methoxychroman-3-yl)-1,3-dihydroimidazole-2-thione;
(R)-5-(2-aminoethyl)-1-(8-methoxychroman-3-yl)-1,3-dihydroimidazole-2-thione;
(R)-5-(2-aminoethyl)-1-(6-fluorochroman-3-yl)-1,3-dihydroimidazole-2-thione;
(R)-5-(2-aminoethyl)-1-(8-fluorochroman-3-yl)-1,3-dihydroimidazole-2-thione;
(R)-5-(2-aminoethyl)-1-(6,7-difluorochroman-3-yl)-1,3-dihydroimidazole-2-thione;
(R)-5-(2-aminoethyl)-1-(6,8-difluorochroman-3-yl)-1,3-dihydroimidazole-2-thione;
(S)-5-(2-aminoethyl)-1-(6,8-difluorochroman-3-yl)-1,3-dihydroimidazole-2-thione;
(R)-5-(2-aminoethyl)-1-(6,7,8-trifluorochroman-3-yl)-1,3-dihydroimidazole-2-thione;
(R)-5-(2-aminoethyl)-1-(6-chloro-8-methoxychroman-3-yl)-1,3-dihydroimidazole-2-thione;
(R)-5-(2-aminoethyl)-1-(6-methoxy-8-chlorochroman-3-yl)-1,3-dihydroimidazole-2-thione;
(R)-5-(2-aminoethyl)-1-(6-nitrochroman-3-yl)-1,3-dihydroimidazole-2-thione;
(R)-5-(2-aminoethyl)-1-(8-nitrochroman-3-yl)-1,3-dihydroimidazole-2-thione;

(R)-5-(2-aminoethyl)-1-[6-(acetylamino)chroman-3-yl]-1,
3-dihydroimidazole-2-thione;
(R)-5-aminomethyl-1-chroman-3-yl-1,3-dihydroimidazole-
2-thione;
(R)-5-aminomethyl-1-(6-hydroxychroman-3-yl)-1,3-dihydroimidazole-2-thione;
(R)-5-(2-aminoethyl)-1-(6-hydroxy-7-benzylchroman-3-yl)-1,3-dihydroimidazole-2-thione;
(R)-5-aminomethyl-1-(6,8-difluorochroman-3-yl)-1,3-dihydroimidazole-2-thione;
(R)-5-(3-aminopropyl)-1-(6,8-difluorochroman-3-yl)-1,3-dihydroimidazole-2-thione;
(S)-5-(3-aminopropyl)-1-(5,7-difluoro-1,2,3,4-tetrahydronaphthalen-2-yl)-1,3-dihydroimidazole-2-thione;
(R,S)-5-(2-aminoethyl)-1-(6-hydroxythiochroman-3-yl)-1,
3-dihydroimidazole-2-thione;
(R,S)-5-(2-aminoethyl)-1-(6-methoxythiochroman-3-yl)-1,
3-dihydroimidazole-2-thione;
(R)-5-(2-benzylaminoethyl)-1-(6-methoxychroman-3-yl)-1,
3-dihydroimidazole7-2-thione;
(R)-5-(2-benzylaminoethyl)-1-(6-hydroxychroman-3-yl)-1,
3-dihydroimidazole-2-thione;
(R)-1-(6-hydroxychroman-3-yl)-5-(2-methylaminoethyl)-1,
3-dihydroimidazole-2-thione;
(R)-1-(6,8-difluorochroman-3-yl)-5-(2-methylaminoethyl)-
1,3-dihydroimidazole-2-thione;
(R)-1-chroman-3-yl-5-(2-methylaminoethyl)-1,3-dihydroimidazole-2-thione; or
(R)-5-(2-(benzylamino)ethyl)-1-(6,8-difluorochroman-3-yl)-1H-imidazole-2(3H)-thione.

The compounds above may suitably be provided in the form of a pharmaceutically acceptable salt, preferably the hydrochloride salt.

In an embodiment, there is provided (R)-5-(2-aminoethyl)-1-(6,8-difluorochroman-3-yl)-1,3-dihydroimidazole-2-thione or (R)-5-(2-amino ethyl)-1-(6,8-difluorochroman-3-yl)-1,3-dihydroimidazole-2-thione, or a pharmaceutically acceptable salt thereof, typically the hydrochloride salt, for use in treating pulmonary arterial hypertension. Preferably, there is provided the hydrochloride salt of (R)-5-(2-aminoethyl)-1-(6,8-difluorochroman-3-yl)-1,3-dihydroimidazole-2-thione or (R)-5-(2-aminoethyl)-1-(6,8-difluorochroman-3-yl)-1,3-dihydroimidazole-2-thione for use in treating pulmonary arterial hypertension. The (R)-5-(2-aminoethyl)-1-(6,8-difluorochroman-3-yl)-1,3-dihydroimidazole-2-thione or (R)-5-(2-aminoethyl)-1-(6,8-difluorochroman-3-yl)-1,3-dihydroimidazole-2-thione, or pharmaceutically acceptable salt thereof may be used in combination with one or more active pharmaceutical ingredients, as described below.

In an embodiment, there is provided (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione, or pharmaceutically acceptable salt thereof, typically the hydrochloride salt, for use in treating pulmonary arterial hypertension. Preferably, there is provided (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione (hydrochloride) for use in treating pulmonary arterial hypertension. The (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione, or pharmaceutically acceptable salt thereof may be used in combination with one or more active pharmaceutical ingredients, as described below.

The preparation of compounds of formula I is described in WO2004/033447 and WO2008/136695.

Reference is made to the "Guidelines for the diagnosis and treatment of pulmonary hypertension" (European Heart Journal (2009) 30, 2493-2537) for details on the definition, classification and pathology and pathobiological features of PAH.

Typically, pulmonary hypertension is a group of diseases characterized by a progressive increase of pulmonary vascular resistance leading to right ventricular failure and premature death. It may be defined by a mean pulmonary artery pressure greater than 25 mmHg at rest.

PAH has been clinically classified by the WHO into 5 groups, according to the cause of the disease, and symptoms may differ, depending on the 'group' that caused the disease. However, 'common' symptoms are as follows:
Difficulty in breathing or shortness of breath (main symptom)
Fatigue
Dizziness
Swelling in the ankles or legs (edema)
Bluish lips and skin (cyanosis)
Chest pain
Racing pulse and palpitations A clinical classification of PAH has been undertaken and reported by Simonneau G et al in "Updated clinical classification of pulmonary hypertension", J Am Coll Cardiol 2009; 54:S43-S54. PAH was classified as follows:

Clinical Classification of Pulmonary Arterial Hypertension (PAH):
1.1 Idiopathic
1.2 Heritable
   1.2.1 Bone morphogenetic protein receptor type II (BMPR2)
   1.2.2 Activin receptor-like kinase-1 (ALK1), endoglin (with or without hereditary haemorrhagic telangiectasia)
   1.2.3 Unknown
1.3 Drugs and toxins induced
1.4 Associated with (Associated PAH, APAH)
   1.4.1 Connective tissue diseases
   1.4.2 HIV infection
   1.4.3 Portal hypertension
   1.4.4 Congenital heart disease
   1.4.5 Schistosomiasis
   1.4.6 Chronic haemolytic anaemia
1.5 Persistent pulmonary hypertension of the newborn The WHO has also provided the following functional assessment classification:

| Functional Class | Symptomatic profile |
| --- | --- |
| I | Patients with pulmonary hypertension but without resulting limitation of physical activity. Ordinary physical activity does not cause dyspnoea or fatigue, chest pain, or near syncope |
| II | Patients with pulmonary hypertension resulting in slight limitation of physical activity. They are comfortable at rest. Ordinary physical activity causes undue dyspnoea or fatigue, chest pain, or near syncope |
| III | Patients with pulmonary hypertension resulting in marked limitation of physical activity. They are comfortable at rest. Less than ordinary activity causes undue dyspnoea or fatigue, chest pain, or near syncope |
| IV | Patients with pulmonary hypertension with inability to carry out any physical activity without symptoms. These patients manifest signs of right heart failure. Dyspnoea and/or fatigue may even be present at rest. Discomfort is increased by any physical activity |

In an embodiment, the present invention relates to a compound of formula I in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione (hydrochloride), whether alone or in combination with one or more other active pharmaceutical ingredients (APIs), for use in treating one or more of the above classes of PAH. The PAH may be characterised by a mean pulmonary artery pressure greater than 25 mmHg at rest.

In an embodiment, the present invention relates to a compound of formula I in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione (hydrochloride), whether alone or in combination with one or more other active pharmaceutical ingredients, for use in treating one or more of the above classes of PAH. The PAH may be characterised by a mean pulmonary artery pressure greater than 25 mmHg at rest.

As used herein, the term treatment and variations such as 'treat' or 'treating' refer to any regime that can benefit a human or non-human animal. The treatment may be in respect of an existing condition or may be prophylactic (preventative treatment). Treatment may include curative, alleviation or prophylactic effects. The treatment may also involve curing, alleviating or preventing symptoms associated with the disorder rather than acting on the underlying cause of the disorder. Treatment with a compound of formula I in combination with one of the other classes of compounds includes simultaneous and sequential administration of the two or more drugs.

The expected beneficial therapeutic effects of the compounds of formula I in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione (hydrochloride) in treating pulmonary arterial hypertension have been described above. It will be appreciated that the compounds of formula I in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione (hydrochloride) may also exhibit beneficial therapeutic effects in treating conditions associated with PAH, for example conditions exhibiting lung injury. Such conditions include breathing difficulties, shortness of breath, fatigue, dizziness, swelling in the ankles or legs (oedema), bluish lips and skin (cyanosis), chest pain, racing pulse and palpitations Treatment of such conditions with compounds of formula I, in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione, or pharmaceutically acceptable salts thereof forms another aspect of the present invention. Thus, the present invention provides a compound of formula I in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione, or a pharmaceutically acceptable salt thereof for use in treating lung injury. Suitably, the present invention provides a compound of formula I in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione, or a pharmaceutically acceptable salt thereof for use in treating one or more of the following conditions: breathing difficulties, shortness of breath, fatigue, dizziness, swelling in the ankles or legs (oedema), bluish lips and skin (cyanosis), chest pain, racing pulse and palpitations.

Clinical trials may be undertaken in order to demonstrate the therapeutic efficacy of a compound of formula I, in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione (hydrochloride), whether alone or in combination with one or more other active pharmaceutical ingredients, in treating PAH. Preferably, the clinical trial is a randomised controlled trial; suitably the trial being a double-blind trial.

According to another aspect of the present invention, there is provided a method of treating pulmonary arterial hypertension comprising administering a therapeutically effective amount of a compound of formula I, in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione, or a pharmaceutically acceptable salt thereof as described above to a subject in need thereof, optionally in combination with another API such as one listed below. The PAH may be characterised by a mean pulmonary artery pressure greater than 25 mmHg at rest.

According to another aspect of the present invention, there is provided a method of treating lung injury comprising administering a therapeutically effective amount of a compound of formula I, in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione, or a pharmaceutically acceptable salt thereof as described above to a subject in need thereof, optionally in combination with another API such as one listed below. Suitably, the present invention provides a method of treating one or more of the following conditions: breathing difficulties, shortness of breath, fatigue, dizziness, swelling in the ankles or legs (oedema), bluish lips and skin (cyanosis), chest pain, racing pulse and palpitations comprising administering a therapeutically effective amount of a compound of formula I, in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione, or a pharmaceutically acceptable salt thereof as described above to a subject in need thereof, optionally in combination with another API such as one listed below.

According to another aspect of the present invention, there is provided the use of a compound of formula I, in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione, or a pharmaceutically acceptable salt thereof as described above, optionally in combination with another API such as one listed below, in the manufacture of a medicament for treating pulmonary arterial hypertension. The PAH may be characterised by a mean pulmonary artery pressure greater than 25 mmHg at rest.

According to another aspect of the present invention, there is provided the use of a compound of formula I, in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione, or a pharmaceutically acceptable salt thereof as described above, optionally in combination with another API such as one listed below, in the manufacture of a medicament for treating lung injury. Suitably, the present invention provides the use of a compound of formula I, in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione, or a pharmaceutically acceptable salt thereof as described above, optionally in combination with another API such as one listed below, in the manufacture of a medicament for treating one or more of the following: breathing difficulties, shortness of breath, fatigue, dizziness, swelling in the ankles or legs (oedema), bluish lips and skin (cyanosis), chest pain, racing pulse and palpitations.

The compound of formula I, in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione, or a pharmaceutically acceptable salt thereof, suitably for use as described above, may be formulated into a pharmaceutical composition, optionally in combination with another API such as one listed below.

For the preparation of pharmaceutical compositions of compounds of formula I, in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione (hydrochloride), inert pharmaceutically acceptable carriers are admixed with the active compounds. The pharmaceutically acceptable carriers may be either solid or liquid. Solid form preparations include powders, tablets, dispersible granules and capsules. A solid carrier can be one or more substances which may also act as diluents, flavouring agents, solubilizers, lubricants, suspending agents, binders or tablet disintegrating agents; it may also be an encapsulating material.

Preferably the pharmaceutical composition is in unit dosage form, e.g. packaged composition, the package containing discrete quantities of the composition such as packeted tablets, capsules and powders in vials or ampoules. The dosages may be varied depending on the requirement of the patient, the severity of the disease and the particular compound being employed. For convenience, the total daily dosage may be divided and administered in portions throughout the day. It is expected that once or twice per day administration will be most suitable.

When the compound of formula I is in the form of Compound B ((R)-5-(2-(benzylamino)ethyl)-1-(6,8-difluorochroman-3-yl)-1H-imidazole-2(3H)-thione), the dose of Compound B is in the range of about 10 mg/day to about 50 mg/day, preferably in the range of about 15 mg/day to about 45 mg/day, more preferably in the range of about 20 mg/day to about 40 mg/day, most preferably in the range of about 25 mg/day to about 35 mg/day typically about 30 mg/day. Preferably, the Compound B is in the form of a single daily dosage. The present invention thus also provides a pharmaceutical composition comprising Compound B in the amount described above for use in treating PAH. The PAH may be characterised by a mean pulmonary artery pressure greater than 25 mmHg at rest.

The composition may further comprise another active pharmaceutical ingredient. Suitable active ingredients are described in WO2007/081232 and WO2008/136695.

The compound of formula I, in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione (hydrochloride), may be used in conjunction with another active pharmaceutical ingredient, i.e. with one or more other classes of compounds. The compound of formula I, in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione (hydrochloride), may be used in simultaneous or sequential administration. For simultaneous administration the compound of formula I, in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione (hydrochloride), may be incorporated into the same composition as a fixed dose composition, as noted above, or may be administered as two separate compositions. Suitable active ingredients are described in WO2007/081232 and WO2008/136695.

Typically, the other active ingredient is selected from the following one or more of the following classes:
diuretics; beta-adrenergic antagonists; alpha2-adrenergic agonists; alpha1-adrenergic antagonists; dual beta- and alpha-adrenergic antagonists; calcium channel blockers; potassium channel activators; anti-arrhythmics; ACE inhibitors; angiotensin (e.g. AT1) receptor antagonists; renin inhibitors; lipid lowerers, vasopeptidase inhibitors; nitrates; endothelin antagonists/endothelin receptor inhibitors; neutral endopeptidase inhibitors; anti-angiotensin vaccines; vasodilators; phosphodiesterase inhibitors; cardiac glycosides; serotonin antagonists; CNS acting agents; calcium sensitisers; HMG CoA reductase inhibitors; vasopressin antagonists; adenosine A1 receptor antagonists; atrial natriuretic peptide (ANP) agonists; chelating agents; corticotrophin-releasing factor receptor; glucagon-like peptide-1 agonists; sodium, potassium ATPase inhibitors; advanced glycosylation end-products (AGE) crosslink breakers; mixed neprilysin/endothelin-converting enzyme (NEP/ECE) inhibitors; nociceptin receptor (ORL-1) agonists (e.g. alprazolam); xanthine oxidase inhibitors; benzodiazepine agonists; cardiac myosin activators; chymase inhibitors; endothelial nitric oxide synthase (ENOS) transcription enhancers; and neutral endopeptidase inhibitors such as thiorphan, in particular angiotensin receptor antagonists, phosphodiesterase inhibitors and endothelin receptor inhibitors.

The invention also envisages the use of nepicastat with the classes of compounds described above.

The other active ingredient may be selected from one or more of the following: epoprostenol (for example continuously injected through an intravenous (IV) catheter), iloprost (for example inhaled), bosentan, ambrisentan, sitaxentan, sildenafil, tadalafil, amlodipine, felodipine, diltiazem, nifedipine, nicardipine isosorbide dinitrate, isosorbide-5-mononitrate, warfarin, captopril, enalapril, lisinopril, benazepril, fosinopril, trandolapril, quinapril, ramipril, perindopril, zofenopril, cilazapril, imidapril, losartan, candersartan, olmesartan, irbesartan, eprosartan, telmisartan, valsartan, acetazolamide, dichlorphenamide, methazolamide, furosemide, ethacrynic acid, torasemide (torsemide), azosemide (axosemide), piretanide, tripamide, hydrochlorothiazide, chlorothiazide, bendroflumethiazide, methyclothiazide, polythiazide, trichlormethiazide, chlorthalidone, indapamide, metolazone, quinethazone, amiloride, triamterene, spironolactone, canrenone, potassium canrenoate and eplerenone. Suitably, one of the above other active ingredients is combined with the compound of formula I, in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione (hydrochloride).

Other APIs used in treating pulmonary arterial hypertension may also be combined with the compound of formula I.

In an embodiment, the compound of formula I, in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione (hydrochloride), is used in combination with an endothelin antagonist. Suitably, the endothelin antagonist is bosentan, sitaxentan or ambrisentan.

In an embodiment, the compound of formula I, in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione (hydrochloride), is used in combination with a prostacyclin analogue. Suitably, the prostacyclin analogue is selected from epoprostenol (for example continuously injected through an intravenous (IV) catheter), iloprost (for example inhaled), treprostinil and beraprost.

In an embodiment, the compound of formula I, in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione (hydrochloride), is used in combination with a phosphodiesterase type-5 (PDE-5) inhibitor. Suitably, the PDE-5 inhibitor is selected from sildenafil and tadalafil.

In an embodiment, the compound of formula I, in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione (hydrochloride), is used in combination with a calcium channel blocker (CCB). Suitably, the CCB is selected from nifedipine, dilitiazem, amlodipine and felodipine.

According to another aspect of the present invention, there is provided a pharmaceutical composition comprising a compound of formula I, in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione, or a pharmaceutically acceptable salt thereof as described above and an endothelin antagonist. Suitably, the endothelin antagonist is bosentan. The pharmaceutical combination may also include one or more inert pharmaceutically acceptable carriers.

In an embodiment, there is provided a pharmaceutical combination comprising a compound of formula IA or a pharmaceutically acceptable salt thereof as described above and an endothelin antagonist. Preferably, the combination comprises (R)-5-(2-aminoethyl)-1-(6,8-difluorochroman-3-yl)-1,3-dihydroimidazole-2-thione hydrochloride and an endothelin antagonist. More preferably, the combination comprises (R)-5-(2-aminoethyl)-1-(6,8-difluorochroman-3-yl)-1,3-dihydroimidazole-2-thione hydrochloride and bosentan. The pharmaceutical combination may also include one or more inert pharmaceutically acceptable carriers.

In an embodiment, there is provided a pharmaceutical combination comprising a compound of formula IB or a pharmaceutically acceptable salt thereof as described above and an endothelin antagonist. Preferably, the compound of formula IB is a compound of formula (R)—B. More preferably, the combination comprises (R)-5-(2-(benzylamino)ethyl)-1-(6,8-difluorochroman-3-yl)-1H-imidazole-2(3H)-thione and an endothelin antagonist. Most preferably, the combination comprises (R)-5-(2-(benzylamino)ethyl)-1-(6,8-difluorochroman-3-yl)-1H-imidazole-2(3H)-thione and bosentan. The pharmaceutical combination may also include one or more inert pharmaceutically acceptable carriers.

Preferably the pharmaceutical composition comprising the combination of the compound of formula I and the other active pharmaceutical ingredient is in unit dosage form, e.g. packaged composition, the package containing discrete quantities of the composition such as packeted tablets, capsules and powders in vials or ampoules. Preferably, the compound of formula I in combination with the other active pharmaceutical ingredient is in the form of a single daily dosage, i.e. a unit dosage form to be administered once a day.

When the compound of formula IB is in the form of Compound B ((R)-5-(2-(benzylamino)ethyl)-1-(6,8-difluorochroman-3-yl)-1H-imidazole-2(3H)-thione), the dose of Compound B may be in the range of about 10 mg/day to about 50 mg/day, preferably in the range of about 15 mg/day to about 45 mg/day, more preferably in the range of about 20 mg/day to about 40 mg/day, most preferably in the range of about 25 mg/day to about 35 mg/day typically about 30 mg/day. When the Compound B is combined with bosentan, the bosentan may be in the range of about 50 mg/day to about 350 mg/day, preferably in the range of about 75 mg/day to about 325 mg/day.

The dose of bosentan in the pharmaceutical composition comprising a combination of Compound B and bosentan may be in the in the range of about 80 mg/day to about 120 mg/day, most preferably in the range of about 90 mg/day to about 110 mg/day typically about 100 mg/day. Thus, in one embodiment, the dosages of Compound B and bosentan may be: Compound B in the range of about 10 mg/day to about 50 mg/day; and bosentan in the range of about 80 mg/day to about 120 mg/day.

The dose of bosentan in the pharmaceutical composition comprising a combination of Compound B and bosentan may be in the in the range of about 280 mg/day to about 320 mg/day, most preferably in the range of about 290 mg/day to about 310 mg/day typically about 300 mg/day. Thus, in one embodiment, the dosages of Compound B and bosentan may be: Compound B in the range of about 10 mg/day to about 50 mg/day; and bosentan in the range of about 280 mg/day to about 320 mg/day.

Preferably, the Compound B and bosentan is in the form of a single daily dosage. The present invention thus also provides a pharmaceutical composition comprising Compound B and bosentan in the amounts described above for use in treating PAH. The PAH may be characterised by a mean pulmonary artery pressure greater than 25 mmHg at rest.

According to another aspect of the present invention, there is provided a pharmaceutical composition comprising a compound of formula I, in particular, (R)-5-(2-(benzylamino)ethyl)-1-(6,8-difluorochroman-3-yl)-1H-imidazole-2(3H)-thione or (R)-5-(2-aminoethyl)-1-(6,8-difluorochroman-3-yl)-1,3-dihydroimidazole-2-thione, or a pharmaceutically acceptable salt thereof as described above and phosphodiesterase type-5 (PDE-5) inhibitor. Suitably, the phosphodiesterase type-5 (PDE-5) inhibitor is sildenafil. The pharmaceutical combination may also include one or more inert pharmaceutically acceptable carriers.

In an embodiment, there is provided a pharmaceutical combination comprising a compound of formula IA or a pharmaceutically acceptable salt thereof as described above and an endothelin antagonist. Preferably, the combination comprises (R)-5-(2-aminoethyl)-1-(6,8-difluorochroman-3-yl)-1,3-dihydroimidazole-2-thione hydrochloride and phosphodiesterase type-5 (PDE-5) inhibitor. More preferably, the combination comprises (R)-5-(2-aminoethyl)-1-(6,8-difluorochroman-3-yl)-1,3-dihydroimidazole-2-thione hydrochloride and sildenafil. The pharmaceutical combination may also include one or more inert pharmaceutically acceptable carriers.

In an embodiment, there is provided a pharmaceutical combination comprising a compound of formula IB or a pharmaceutically acceptable salt thereof as described above and an endothelin antagonist. Preferably, the compound of formula IB is a compound of formula (R)—B. More preferably, the combination comprises (R)-5-(2-(benzylamino)ethyl)-1-(6,8-difluorochroman-3-yl)-1H-imidazole-2(3H)-thione and a phosphodiesterase type-5 (PDE-5) inhibitor. Most preferably, the combination comprises (R)-5-(2-(benzylamino)ethyl)-1-(6,8-difluorochroman-3-yl)-1H-imidazole-2(3H)-thione and sildenafil. The pharmaceutical combination may also include one or more inert pharmaceutically acceptable carriers.

BRIEF DESCRIPTION OF THE DRAWINGS

Reference is now made to the accompanying Figures, in which:

FIG. 4—Ratios of heart weight over bodyweight (BW) (FIG. 4a) and Fulton index (RV/LF+S) (FIG. 4b) from MCT (●), MCT+Bos300 (■), MCT+Bos100 (▲), MCT+Compound B (▼), MCT+Compound B+Bos100 (♦), SHAM (○) and SHAM+Compound B (□) treated rats at 28 days after MCT or vehicle (Sham) administration. Data represents means±sem of n=4-14. Significantly different from MCT (*P<0.05) or from Sham and Sham+Compound B (# P<0.05).

FIG. 5—Ratios of right ventricle (RV) (FIG. 5a) and left ventricle plus septum (LV/S) weight over bodyweight (BW) (FIG. 5b) from MCT (●), MCT+Bos300 (■), MCT+Bos100 (▲), MCT+Compound B (▼), MCT+Compound B+Bos100 (♦), SHAM (○) and SHAM+Compound B (□) treated rats at 28 days after MCT or vehicle (Sham) administration. Data represents means±sem of n=4-14. Significantly different from MCT (*P<0.05) or from Sham and Sham+Compound B (# P<0.05).

Materials and Methods
In Vivo Studies

One of the most-used animal models is the Monocrotaline (MCT) lung injury model of Pulmonary Arterial Hypertension. Administration of MCT, that is metabolized in the liver to the reactive metabolite dehydromonocrotaline, results in a syndrome characterized by acute lung injury, interstitial pulmonary fibrosis, necrotizing pulmonary arteritis, pulmonary hypertension, right ventricular (RV) hypertrophy, myocarditis and hepatic venoocclusive disease.

Experimental Procedure

The Monocrotaline (MCT) Lung Injury Model of Pulmonary Arterial Hypertension Set Up The protocol to use is a standard one (Curr. Protoc. Pharmacol. 46:5.56.1-5.56.11 (2009) John Wiley & Sons Inc). Rats, of 6-7 weeks old (150-200 g) are administered MCT 60 mg/kg subcutaneously, and the pathology usually develops in the course of initial 3 to 4 weeks with the animals dying within the next 2 weeks ($5^{th}$-$6^{th}$ week). A decrease of 50% in food and water consumption is thought to be indicative of pathological status severe enough for testing.

Experimental Design

Figure 1:
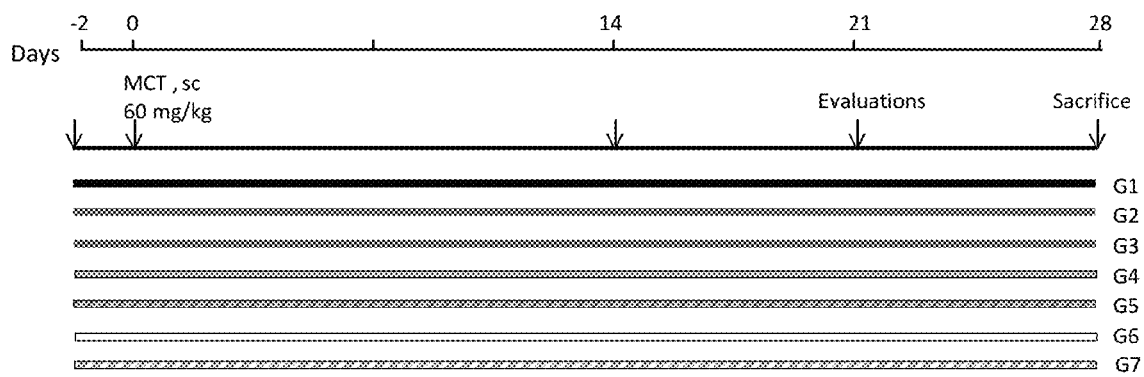
FIG. 1—represents a schematic of the study described below.

Two studies were conducted separately and a combination analysis performed on the two studies. Each study consisted in the scheme represented in FIG. 1.

Compound B refers to (R)-5-(2-benzylamino)ethyl)-1-(6,8-difluorochroman-3-yl)-1H-imidazole-2(3H)-thione (i.e. compound (R)—B as shown above). The structure is as follows:

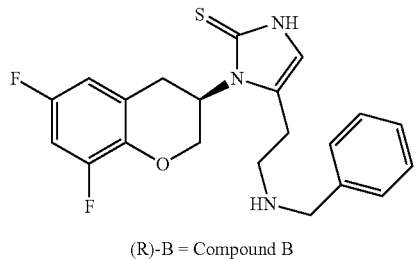 [SMILES: Fc1cc(F)c2c(c1)C[C@@H](n1c(CCNCc3ccccc3)c[nH]c1=S)CO2]

(R)-B = Compound B

The treatment groups for each study were as follows.

| Group | Treatment | n |
| --- | --- | --- |
| G1 | MCT + Vehicle | 10 |
| G2 | MCT + Bosentan 300 mg/kg | 10 |
| G3 | MCT + Bosentan 100 mg/kg | 10 |
| G4 | MCT + Compound B 30 mg/kg | 10 |
| G5 | MCT + Compound B 30 mg/kg + Bosentan 100 mg/kg | 10 |
| G6 | Vehicle SHAM | 6 |
| G7 | Compound B 30 mg/kg SHAM | 6 |

Compound B was obtained from Bial-Portela & Ca., S.A. Monocrotaline was obtained from *Sequoia* Research Products Limited. Bosentan (CAS number 157212-55-0) was obtained from APICHEM.

Abbreviations:
a. Bos=Bosentan
b. Bos100=Bosentan 100 mg/kg
c. Bos300=Bosentan 300 mg/kg
d. LV+S=Left ventricle+septum
e. MCT=Monocrotaline
f. RV=Right ventricle The experimental design of both studies was the same, with animals randomized in seven groups, five groups of 10 animals each (MCT, MCT+Bos300, MCT+Bos100, MCT+Compound B, MCT+Compound B+Bos100) and 2 groups of 6 animals each (SHAM and SHAM+Compound B).

The experimental details are described in more detail below; briefly, compounds were given to rats mixed with food starting, Compound B (30 mg/kg/day) for groups MCT+Compound B and SHAM+Compound B, bosentan (300 mg/kg/day) for group MCT+Bos300, bosentan (100 mg/kg/day) for group MCT+Bos100, Compound B+bosentan (30+100 mg/kg/day) for group MCT+Compound B+Bos100, and no compound for groups MCT and SHAM. Animals from groups MCT were administered MCT and animals from groups SHAM were administered vehicle. Twenty eight days later, surviving animals were sacrificed, tissues collected and weighed. During the entire experimental period food, water consumption and animal weight were monitored. The ratios organ weight to body weight (BW) were calculated to evaluate organ hypertrophy. The index of RV/LV+S was calculated as an index of RV hypertrophy. In each study an n=10 animals was used for each MCT treatment group, and an n=6 was used for the groups not given MCT. The animals from MCT+Bos300 group from Study 1 were not considered for the combined survival analysis since these unexpectedly presented a higher mortality effect as compared to the MCT group. The surviving animals from this group were nevertheless considered for the cardiac remodelling analysis.

Administration volumes: 3 ml/kg for subcutaneous administration.

Storage conditions: The substances will be stored according to conditions defined in the respective certificate of analysis.

Data Acquisition and Analysis

Raw data acquisition was performed with Gilson Uni-Point™ System Software version 5.11. All data analysis was performed using Prism 5 for Windows software, version 5.02 (GraphPad Software Inc., San Diego, Calif.).

Statistical Analysis

All data is expressed as mean±sem (Standard Error of the Mean) unless otherwise indicated. Differences between treatment groups were analysed by one-way ANOVA and post-hoc Newman-Keuls multiple comparison test. $P<0.05$ was considered statistically significant.

Survival curves were derived by the product limit method of Kaplan and Meier, and compared using the logrank (Mantel Cox) test.

Study 1—Further Details

Animals were given powdered food for an adaptation period of 3-5 days before treatment start. Compounds were given to rats mixed with food (powdered diet) starting on day −2. Forty-eight hours later, on day zero animals from groups G1 through G5 were administered MCT subcutaneously (60 mg/kg) while remaining groups (G6 and G7) were given vehicle instead of MCT. Treatment was prolonged for 28 days. Food, water consumption and animal weight were monitored over the entire duration of the experiment.

On day 28 surviving animals were sacrificed and the following tissues/organs collected and weighed: liver, kidney, lung, heart and spleen. Femurs were removed and measured. Heart was dissected into right ventricle, left ventricle+septum and these were also weighed. The ratio organ to body weight (BW) was calculated as well as the ratio organ weight to femur length. The index of RV/LV+S is an index of RV hypertrophy. Catecholamines were evaluated only on right ventricle and left ventricle+septum.

Six weeks old male Wistar rats (151-187 g) were obtained from Harlan (Spain). Rats were kept 5 per cage, under controlled environmental conditions (12 hr light/dark cycle and room temperature 22±1° C.).

All animal groups were fed powdered food, MCT (G1, n=10) and SHAM (G6, n=6) were given normal food and all other groups were given food mixed with the compounds: MCT-Bos300 (G2, n=10) received food with 300 mg/kg/day bosentan, MCT-Bos100 (G3, n=10) received food with 100 mg/kg/day bosentan, MCT-1058 (G4, n=10) received food with 30 mg/kg/day BIA 5-1058, MCT-1058-Bos100 (G5, n=10) received food with 100 mg/kg/day bosentan plus 30 mg/kg/day BIA 5-1058 and SHAM-1058 (G7, n=6) received food with 30 mg/kg/day BIA 5-1058.

Forty eight hours later animals groups 1 through 5 were administered MCT (60 mg/kg) and groups 6 and 7 were administered vehicle subcutaneously in a volume of 3 ml/kg.

MCT was prepared by dissolving at 300 mg/kg in 1M HCl, neutralizing with 1 M NaOH and diluting to 20 mg/ml with sterile water.

Water and food consumption for each cage and weights of the individual animals were measured twice a week.

Animals were kept under treatment for 28 days after MCT administration. The animals that survived were, at that time, anaesthetized with pentobarbital 60 mg/kg administered intraperitoneally, and subjected to tissue and organ collection.

Whole spleen, whole liver, left kidney and lungs were removed, cleaned and weighed. Heart was removed, cleaned from atria and vascular tissue and weighed. Right ventricle was then dissected from the rest of the heart (left ventricle+septum) and both were weighed and put in tubes containing 0.2 M PCA. Femurs were removed, cleaned and length measured with a calliper.

The ratios organ weight to body weight and organ weight to femur length were calculated as well as the ratio right ventricular weight to left ventricular+septum weight.

Tissues were left in 0.2 M PCA (perchloric acid) for 24 h in the dark at 4° C. and were then frozen at −80° C. Catecholamines were measured in right ventricle and left ventricle+septum.

Catecholamines Quantification

Reagents and Materials: All reagents were obtained from Sigma-Aldrich. SPE columns Sep-Pak® Vac Alumina A cartridge 1 cc/100 mg 50-300 im 100/box were obtained from Waters.

Tissues: Frozen tissues in 0.2 M PCA were thawed, the liquid phase removed, and filtered through 0.22 μm Spin-X filters (Corning Costar) by centrifugation in microfuge for 10 minutes at ~5000 rpm, 4° C. Noradrenaline and dopamine were quantified in filtrates by high-pressure liquid chromatography with electrochemical detection (HPLC-ED).

Test system: Gilson HPLC-ED 142
Test Method: Chromatographic conditions were:
Flow rate: 1 ml/min
Analytical Column: Spheri-5 RP18 5 μm, 4.6×250 mm, Perkin Elmer serial #28918, lot#07H8-1318806
Temperature: Ambient
Injection volume: 50 μl
Mobile phase: 0.15 mM EDTA, 0.1M Sodium acetate, 0.1M Citric acid monohydrate, 1 mM Octyl sulphate, 1.0 mM Dibutylamine, 10% Methanol, pH 3.5 with PCA
Detector set at: Mode Amperometric
0.75 V potential
2 nA sensitivity Study 2—Further Details Animals were given powdered food for an adaptation period of 3-5 days before treatment start. Compounds were given to rats mixed with food (powdered diet) starting on day −2. Forty-eight hours later, on day zero animals from groups G1 through G5 were administered MCT subcutaneously (60 mg/kg) while remaining groups (G6 and G7) were given vehicle instead of MCT. Animal weight, food and water consumption were evaluated twice a week and animals were regularly observed for any disease signs. Mortality was registered and on day 28 surviving animals were sacrificed, selected organs weighed and femurs removed and measured.

Organs weighed were: liver, kidney, lung, heart and spleen. Heart was dissected into right ventricle, left ventricle+septum and these were also weighed. The ratio organ to body weight (BW) was calculated as well as the ratio organ weight to femur length. The index of RV/LV+S is an index of RV hypertrophy.

Rats were housed in groups of 5 in macrolon cages on wood litter with free access to powder chow diet (Code 113—SAFE, 89290 Augy, France) and tap water. The animal house was maintained in a 12-hour light/dark cycle (0700 to 1900 hours) in a controlled ambient temperature of 22±1° C.

Treatment with compound in food started on day −2: for groups G4 and G7 BIA 5-1058 (30 mg/kg/day), for group G2 bosentan (300 mg/kg/day), for group 3 bosentan (100 mg/kg/day), for group 5 BIA 5-1058+bosentan (30+100 mg/kg/day). The remaining animals (groups G1 and G6) were given normal rat chow food. Forty-eight hours later, on day zero, animals from groups G1 through G5 were administered MCT subcutaneously (60 mg/kg/3 ml). Groups G6 and G7 were given vehicle instead of MCT. Treatment was prolonged for 4 weeks.

MCT was dissolved at 300 mg/kg in 1 N HCl, neutralized with 1 N NaOH and diluted to 20 mg/ml with sterile water.

Food, water consumption and animal weight was monitored over the all experiment. Water and food consumption was measured for each cage twice a week. The weights of the individual animals were determined twice a week.

Animals were kept under treatment for 28 days after MCT administration. The animals that survived were, at that time, anaesthetized with pentobarbital 60 mg/kg administered intraperitoneally, and subjected to tissue and organ collection.

Whole spleen, whole liver, both kidneys and lungs were removed, cleaned and weighed. Heart was removed, cleaned from atria and vascular tissue and weighed. Right ventricle was then dissected from the rest of the heart (left ventricle+septum) and both were weighed. Femurs were removed, cleaned and length measured with a calliper.

The ratios organ weight to body weight and organ weight to femur length were calculated as well as the ratio right ventricular weight to left ventricular+septum weight.

Irwin Test

The Irwin test (Irwin S. Psycopharmacologia 1968:13; 222-57) is a systematic observational procedure for assessing and scoring the behavioral and physiological state of rodents. Animals are observed according to a standardised observation battery in order to detect neurobehavioural, neurovegetative or psychotropic signs or neurotoxic effects. A total of 30 parameters are scored using a standardized procedure based on that described by Irwin, 1968. These parameters are distributed as followed: 16 items for the behavioral profile, 9 items for the neurological profile and 5 items for the autonomic profile as represented in Table 1 below:

TABLE 1

| Behavioural | Spontaneous activity | locomotor activity |
| --- | --- | --- |
| | | spatial locomotion |
| | | stereotyped behaviour |
| | | writhing |
| | Motor-affective responses | transfer arousal (appearance) |
| | | touch response |
| | | Provoked biting |
| | | vocalisation |
| | | easy of handling/passivity |
| | Sensoro-motor responses | visual placing reflex |
| | | pain response (tail pinch) |
| | | pain response (toe pinch) |
| | | startle response |
| | Posture | straub tail |
| | | abnormal limb position |
| | | abnormal body carriage |
| | | (posture) |

TABLE 1-continued

| Neurologic | Muscle tone | body tone |
| --- | --- | --- |
| | | abdominal tonus |
| | | limb muscle tonus |
| | | grip strength |
| | Equillibrium and gait | righting reflex |
| | | abnormal gait |
| | | catalepsy |
| | CNS excitability | tremors/twitches/jerks |
| | | convulsions |
| Autonomic | Eyes | ptosis |
| | Secretions | lacrimation |
| | | salivation |
| | General | hypothermia |
| | | piloerection |

Results

Figure 2:
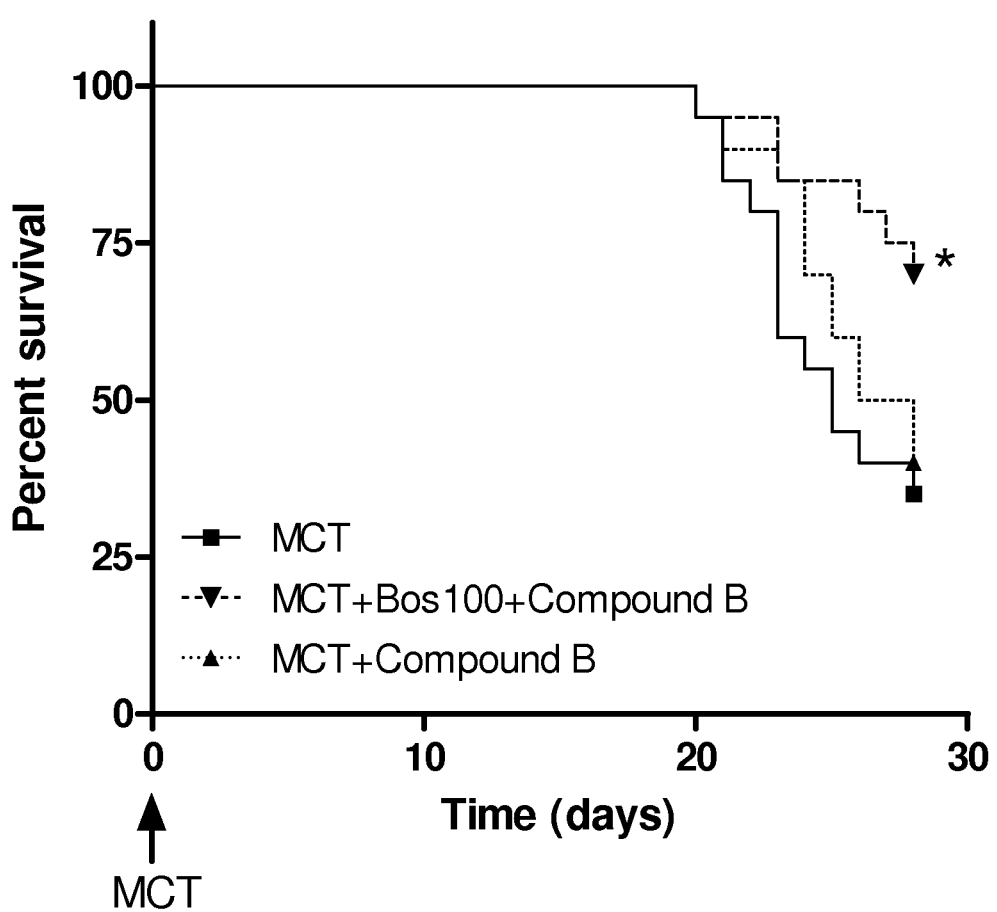
FIG. 2—Kaplan-Meyer survival curves from the day of MCT administration from an initial n=20 of rats in each group of animals.
Figure 3:
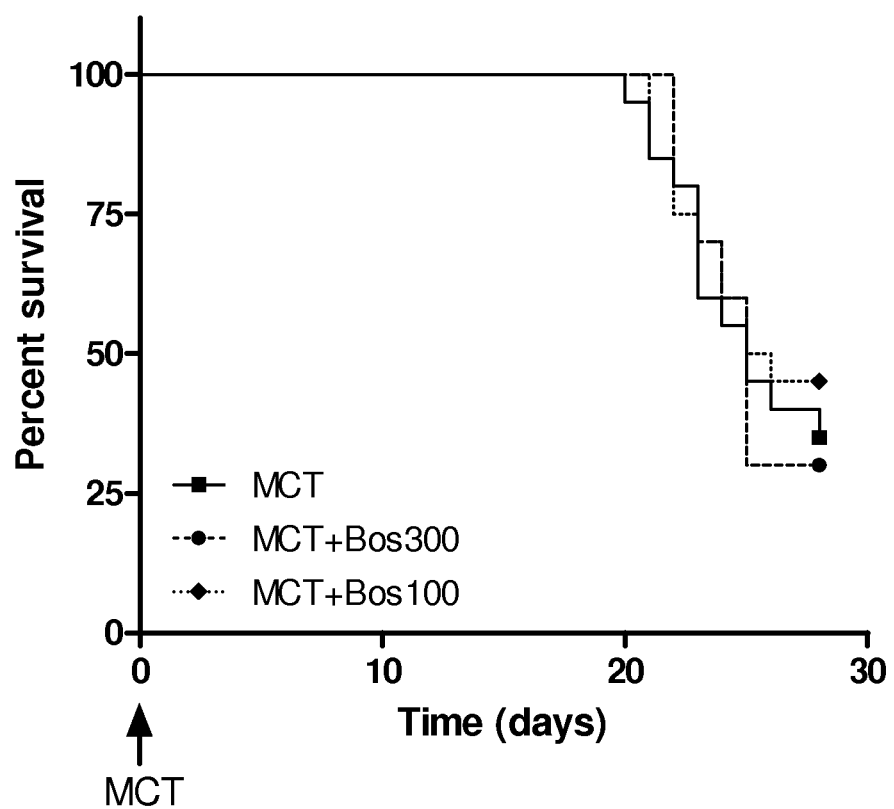
FIG. 3—Kaplan-Meyer survival curves from the day of MCT administration from an initial n=20 of rats in each group of animals, except the MCT+Bos300 (n=10).

Survival curves (see FIGS. 2 and 3) clearly show that the combination of Compound B (30 mg/kg/day) plus bosentan (100 mg/kg/day) significantly (P<0.05) increased the number of animals that survived the 28 days observing period when compared to the MCT group. A slight increase in survival was also observed for the MCT+Compound B group translated by a shift to the right in the survival curve. No clear benefit was observed with either bosentan treatments, 300 or 100 mg/kg/day as compared to the MCT group.

Thus, the use of Compound B alone resulted in greater survival rates compared to the use of bosentan alone. Further, the combined use of Compound B and bosentan resulted in a synergistic effect on survival rates.

No animals died on the SHAM groups.

As shown in FIGS. 4a, 4b, 5a and 5b, Compound B alone or in combination with bosentan significantly decreased the heart, RV and Fulton Index (where the Fulton Index=the ratio of right ventricle weight to left ventricle plus septum weight, i.e. RV/LV+S) as compared to the MCT group; the magnitude of the decrease was higher with the combination Compound B+Bos100 than with the other treatments. Bosentan 300 mg/kg/day significantly decreased the RV and Fulton Index as compared to the MCT group.

All groups administered with MCT had significantly increased heart, RV, LV+S and Fulton Index as compared to SHAM and SHAM+Compound B groups.

Regarding cardiac remodeling a marked and statistically significant decrease in right ventricular hypertrophy was observed in the MCT+Compound B+Bos100 group as compared to the MCT group, similarly to what observed in the MCT+Bos300 group. A significant decreased right ventricular hypertrophy was also observed in the MCT+Bos100 and MCT+Compound B groups.

Thus, Compound B, whether used alone or in combination with bosentan, exhibits beneficial effects in relation to lung injury, particularly pulmonary arterial hypertension.

SYNTHETIC EXAMPLES

Example 1

(R)-5-aminomethyl-1-(6,8-difluorochroman-3-yl)-1,3-dihydroimidazole-2-thione hydrochloride A stirred mixture of (R)-6,8-difluorochroman-3-ylamine hydrochloride (0.22 g, 1.0 mmol), [3-(tert-butyldimethylsilanyloxy)-2-oxopropyl]carbamic acid tert-butyl ester (0.33 g, 1.1 mmol), potassium thiocyanate (0.11 g, 1.1 mmol) and acetic acid (0.3 mL, 5.0 mmol) in ethyl acetate (3 mL) was refluxed for 2 hours, cooled to room temperature, then washed by sodium bicarbonate solution, dried over anhydrous magnesium sulphate and evaporated in vacuo. The residue was purified by the column chromatography over silica gel using ethyl acetate-petroleum ether mixture as eluent. The resulting oil (0.23 g) was dissolved in ethyl acetate (2 ml), whereupon 2M HCl solution in ethyl acetate was added (2 mL, 4 mmol) and the mixture was stirred for 2 hours at room temperature. The precipitate was removed by filtration and washed with ethyl acetate to give crystals of m.p. 192° C. (decomp.).

Example 2

(R)-5-(2-(benzylamino)ethyl)-1-(6,8-difluorochroman-3-yl)-1H-imidazole-2(3H)-thione To (R)-5-(2-aminoethyl)-1-(6,8-difluorochroman-3-yl)-1,3-dihydroimidazole-2-thione (2.36 g, 7.58 mmol) and benzaldehyde (0.85 ml, 8.34 mmol) in a mixture of methanol (15 ml), and dichloromethane (15 ml) sodium cyanoborohydride (0.67 g, 10.66 mmol) was added at 20-25° C. in portions. The mixture was stirred for 64 h, quenched with 1N HCl (12 ml) with stirring followed by 3N NaOH (12 ml). The mixture was extracted with DCM (100 ml), the organic phase was washed with brine (50 ml), dried (MgSO$_4$) and evaporated to dryness. The residue was purified on a silica gel column with ethyl acetate and a mixture of ethyl acetate with methanol (9:1) as eluents. Fractions containing the product were collected, evaporated under reduced pressure to approx 20 ml then cooled on ice. The precipitate was collected, washed with ethyl acetate-petroleum ether (1:1) mixture, dried on air. Yield was 1.25 g (41%), the product having a mp 188-90° C. (2-propanol-DCM).

It will be appreciated that the invention may be modified within the scope of the appended claims.

The invention claimed is:

1. A method of treating pulmonary arterial hypertension comprising administering to a subject in need thereof a therapeutically effective amount of a compound of formula I:

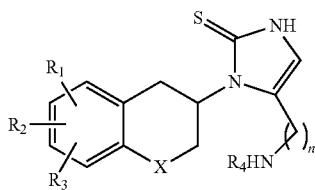

wherein $R_1$, $R_2$ and $R_3$ are the same or different and signify hydrogens, halogens, alkyl, alkylaryl, alkyloxy, hydroxy, nitro, amino, alkylcarbonylamino, alkylamino or dialkylamino group; $R_4$ signifies hydrogen, alkyl, -alkylaryl or -alkylheteroaryl; X signifies CH$_2$, oxygen atom or sulphur atom; n is 1, 2 or 3, with the proviso that when n is 1, X is not CH$_2$; and the individual (R)- and (S)-enantiomers or mixtures of enantiomers and pharmaceutically acceptable salts thereof, optionally in combination with at least one other active pharmaceutical ingredient.

2. The method according to claim 1, wherein the compound of formula I has the formula IA

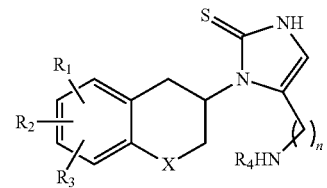

wherein $R_1$, $R_2$ and $R_3$ are the same or different and signify hydrogens, halogens, alkyl, alkylaryl, alkyloxy, hydroxy, nitro, amino, alkylcarbonylamino, alkylamino or dialkylamino group; $R_4$ signifies hydrogen, alkyl or -alkylaryl group; X signifies CH$_2$, oxygen atom or sulphur atom; and n is 1, 2 or 3, with the proviso that when n is 1, X is not CH$_2$.

3. The method according to claim 1, wherein the compound of formula I has the formula IB

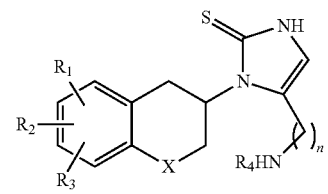

wherein $R_1$, $R_2$ and $R_3$ are the same or different and signify hydrogen, halogen, alkyl, nitro, amino, alkylcarbonylamino, alkylamino or dialkylamino group; $R_4$ signifies -alkyl-aryl or -alkyl-heteroaryl; X signifies CH$_2$, oxygen atom or sulphur atom; and n is 2 or 3.

4. The method according to claim 1, wherein X is O.

5. The method according to claim 1, wherein n is 2 or 3.

6. The method according to claim 1, wherein at least one of $R_1$, $R_2$ and $R_3$ is fluorine.

7. The method according to claim 1, wherein the compound of formula I is provided as the (R) or (S) enantiomer.

8. The method according to claim 7, wherein the compound of formula I is provided as the (R)-enantiomer.

9. The method according to claim 1, wherein the compound of formula I is selected from:
(S)-5-(2-aminoethyl)-1-(1,2,3,4-tetrahydronaphthalen-2-yl)-1,3-dihydroimidazole-2-thione;
(S)-5-(2-aminoethyl)-1-(5,7-difluoro-1,2,3,4-tetrahydronaphthalen-2-yl)-1,3-dihydroimidazole-2-thione;
(R)-5-(2-aminoethyl)-1-chroman-3-yl-1,3-dihydroimidazole-2-thione;
(R)-5-(2-aminoethyl)-1-(6-hydroxychroman-3-yl)-1,3-dihydroimidazole-2-thione;
(R)-5-(2-aminoethyl)-1-(8-hydroxychroman-3-yl)-1,3-dihydroimidazole-2-thione;
(R)-5-(2-aminoethyl)-1-(6-methoxychroman-3-yl)-1,3-dihydroimidazole-2-thione;
(R)-5-(2-aminoethyl)-1-(8-methoxychroman-3-yl)-1,3-dihydroimidazole-2-thione;
(R)-5-(2-aminoethyl)-1-(6-fluorochroman-3-yl)-1,3-dihydroimidazole-2-thione;
(R)-5-(2-aminoethyl)-1-(8-fluorochroman-3-yl)-1,3-dihydroimidazole-2-thione;
(R)-5-(2-aminoethyl)-1-(6,7-difluorochroman-3-yl)-1,3-dihydroimidazole-2-thione;

(R)-5-(2-aminoethyl)-1-(6,8-difluorochroman-3-yl)-1,3-dihydroimidazole-2-thione;
(S)-5-(2-aminoethyl)-1-(6,8-difluorochroman-3-yl)-1,3-dihydroimidazole-2-thione;
(R)-5-(2-aminoethyl)-1-(6,7,8-trifluorochroman-3-yl)-1,3-dihydroimidazole-2-thione;
(R)-5-(2-aminoethyl)-1-(6-chloro-8-methoxychroman-3-yl)-1,3-dihydroimidazole-2-thione;
(R)-5-(2-aminoethyl)-1-(6-methoxy-8-chlorochroman-3-yl)-1,3-dihydroimidazole-2-thione;
(R)-5-(2-aminoethyl)-1-(6-nitrochroman-3-yl)-1,3-dihydroimidazole-2-thione;
(R)-5-(2-aminoethyl)-1-(8-nitrochroman-3-yl)-1,3-dihydroimidazole-2-thione;
(R)-5-(2-aminoethyl)-1-[6-(acetylamino)chroman-3-yl]-1,3-dihydroimidazole-2-thione;
(R)-5-aminomethyl-1-chroman-3-yl-1,3-dihydroimidazole-2-thione;
(R)-5-aminomethyl-1-(6-hydroxychroman-3-yl)-1,3-dihydroimidazole-2-thione;
(R)-5-(2-aminoethyl)-1-(6-hydroxy-7-benzylchroman-3-yl)-1,3-dihydroimidazole-2-thione;
(R)-5-aminomethyl-1-(6,8-difluorochroman-3-yl)-1,3-dihydroimidazole-2-thione;
(R)-5-(3-aminopropyl)-1-(6,8-difluorochroman-3-yl)-1,3-dihydroimidazole-2-thione;
(S)-5-(3-aminopropyl)-1-(5,7-difluoro-1,2,3,4-tetrahydronaphthalen-2-yl)-1,3-dihydroimidazole-2-thione;
(R,S)-5-(2-aminoethyl)-1-(6-hydroxythiochroman-3-yl)-1,3-dihydroimidazole-2-thione;
(R,S)-5-(2-aminoethyl)-1-(6-methoxythiochroman-3-yl)-1,3-dihydroimidazole-2-thione;
(R)-5-(2-benzylaminoethyl)-1-(6-methoxychroman-3-yl)-1,3-dihydroimidazole7-2-thione;
(R)-5-(2-benzylaminoethyl)-1-(6-hydroxychroman-3-yl)-1,3-dihydroimidazole-2-thione;
(R)-1-(6-hydroxychroman-3-yl)-5-(2-methylaminoethyl)-1,3-dihydroimidazole-2-thione;
(R)-1-(6,8-difluorochroman-3-yl)-5-(2-methylaminoethyl)-1,3-dihydroimidazole-2-thione; (R)-1-chroman-3-yl-5-(2-methylaminoethyl)-1,3-dihydroimidazole-2-thione;
(R)-5-(2-(benzylamino)ethyl)-1-(6,8-difluorochroman-3-yl)-1H-imidazole-2(3H)-thione; or a pharmaceutically acceptable salt thereof.

10. The method according to claim 9, wherein the compound of formula I is provided in the form of the hydrochloride salt.

11. The method according to claim 1, wherein the compound of formula I is (R)-5-(2-aminoethyl)-1-(6,8-difluorochroman-3-yl)-1,3-dihydroimidazole-2-thione or a pharmaceutically acceptable salt thereof.

12. The method according to claim 11, wherein the compound of formula I is the hydrochloride salt of (R)-5-(2-aminoethyl)-1-(6,8-difluorochroman-3-yl)-1,3-dihydroimidazole-2-thione.

13. The method according to claim 1, wherein $R_4$ signifies —$CH_2$-aryl or —$CH_2$-heteroaryl.

14. The method according to claim 13, wherein $R_4$ is benzyl.

15. The method according to claim 1, wherein the compound of formula I has the formula X:

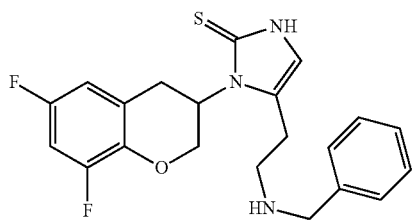

16. The method according to claim 1, wherein the compound of formula I is (R)-5-(2-(benzylamino)ethyl)-1-(6,8-difluorochroman-3-yl)-1H-imidazole-2(3H)-thione or a pharmaceutically acceptable salt thereof.

17. The method according to claim 16, wherein the compound of formula I is (R)-5-(2-(benzylamino)ethyl)-1-(6,8-difluorochroman-3-yl)-1H-imidazole-2(3H)-thione.

18. The method according to claim 1 wherein the at least one other active pharmaceutical ingredient is one or more selected from the following list: epoprostenol, iloprost, bosentan, ambrisentan, sitaxentan, sildenafil, tadalafil, amlodipine, felodipine, diltiazem, nifedipine, nicardipine isosorbide dinitrate, isosorbide-5-mononitrate, warfarin, captopril, enalapril, lisinopril, benazepril, fosinopril, trandolapril, quinapril, ramipril, perindopril, zofenopril, cilazapril, imidapril, losartan, candersartan, olmesartan, irbesartan, eprosartan, telmisartan, valsartan, acetazolamide, dichlorphenamide, methazolamide, furosemide, ethacrynic acid, torasemide (torsemide), azosemide (axosemide), piretanide, tripamide, hydrochlorothiazide, chlorothiazide, bendroflumethiazide, methyclothiazide, polythiazide, trichlormethiazide, chlorthalidone, indapamide, metolazone, quinethazone, amiloride, triamterene, spironolactone, canrenone, potassium canrenoate and eplerenone.

19. A method of treating lung injury including one or more of the following conditions breathing difficulties, shortness of breath, fatigue, dizziness, swelling in the ankles or legs (oedema), bluish lips and skin (cyanosis), chest pain, racing pulse and palpitations comprising administering to a subject in need thereof a therapeutically effective amount of a compound of formula I:

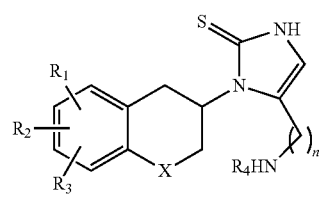

wherein $R_1$, $R_2$ and $R_3$ are the same or different and signify hydrogens, halogens, alkyl, alkylaryl, alkyloxy, hydroxy, nitro, amino, alkylcarbonylamino, alkylamino or dialkylamino group; $R_4$ signifies hydrogen, alkyl or -alkylaryl group or -alkylheteroaryl; X signifies $CH_2$, oxygen atom or sulphur atom; and n is 1, 2 or 3, with the proviso that when n is 1, X is not $CH_2$ and the individual (R)- and (S)-enantiomers or mixtures of enantiomers and pharmaceutically acceptable salts thereof, optionally in combination with at least one other active pharmaceutical ingredient.

* * * * *